US00PP10281P

United States Patent [19]

Olij

[11] Patent Number: Plant 10,281

[45] Date of Patent: Mar. 17, 1998

[54] HYBRID TEA ROSE PLANT NAMED 'OLIJCREM'

[75] Inventor: Huibert W. Olij, De Kwakel, Netherlands

[73] Assignee: Olij Rosen B.V., De Kwakel, Netherlands

[21] Appl. No.: 723,309

[22] Filed: Sep. 30, 1996

[51] Int. Cl.[6] ..... A01H 5/00

[52] U.S. Cl. ..... Plt./15

[58] Field of Search ..... Plt./11, 14, 15, Plt./16

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which forms in great abundance attractive blossoms that are orange-cream in coloration. Such blossoms are long-lasting on the plant or when cut and placed in a vase and exhibit good petal-drop characteristics. The plant exhibits an erect growth habit and forms attractive medium green foliage. Good disease resistance is provided. The new variety is particularly well suited for cut flower production under greenhouse growing conditions.

1 Drawing Sheet

SUMMARY OF THE INVENTION

The new variety of Hybrid Tea rose plant was created by artificial pollnation wherein two parents were crossed which previously had been studied in the hope that they would contribute the desired characteristics. The female parent (i.e., the seed parent) of the new variety was the 'Prophyta' variety (non-patented in the United States). The male parent (i.e., the pollen parent) was the 'Olytel' variety (U.S. Plant Pat. No. 8,862). The parentage of the new variety can be summarized as follows:

'Prophyta'×'Olytel'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characeristics:

(a) forms in great abundance attractive long-lasting blossoms that are orange-cream in coloration,
(b) exhibits an erect growth habit,
(c) forms attractive medium green and glossy foliage,
(d) exhibits good disease resistance, and
(e) is particularly well suited for cut flower production.

The new variety well meets the needs of the horticultural industry and is particularly well adapted for cut flower production under greenhouse growning conditions.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijcrem' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France. Dimensions in centimeters are indicated at the bottom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—reverse;

FIG. 9—illustrates a specimen of a fully open flower—plan view—obverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface; and FIG. 15—illustrates a specimen of a leaf with five leaflets—plan view—under surface.

DETAILED DESCRIPTION

Figures 1, 2, 3, 4, 5, 6, 7, 8, 9, 10, 11, 12, 13, 14, 15:
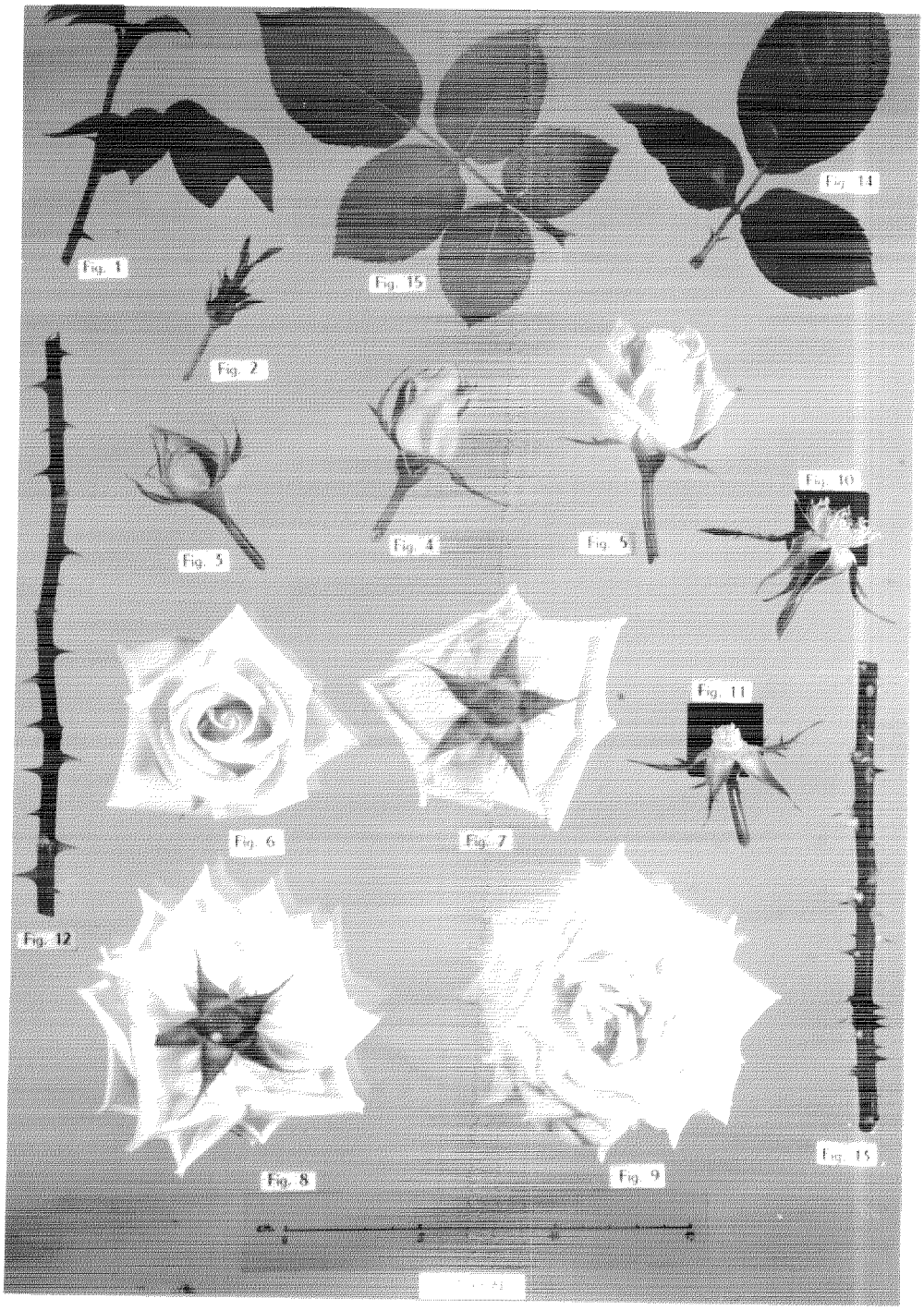

The chart used in the identification of the colors is that of The Royal Horticultural Society (R.H.S. Colour Chart). The description is based on the observation of three year-old plants during June while budded on *Rosa indica* understock and growing in greenhouses at Le Cannet des Maures, Var, France. The coloration in common terms precedes reference to the chart in some instances.

Class: Hybrid Tea.

Plant:

*Height.*—When pruned to a height of 85 cm., floral stems of approximately 40 to 70 cm. in length commonly are formed.

*Habit.*—Erect.

Branches:

*Color.*—Young stems: Yellow-Green, Group 143A. Adult wood: Green Group 137B.

*Thorns.*—Size: medium. Quantity: numerous. Color: greenish to yellow-brown (as illustrated).

Leaves:

*Stipules.*—Adnate, pectinate, narrow and linear.

*Petioles.*—Upper surface: striped reddish brown on young foliage, and dark green on adult foliage. Under surface: light green, with numerous small thorns.

*Leaflets.*—Number: 3, 5 (most often), and 7. Shape: oval. Serration: single and regular. Texture: consistent. General appearance: dense, medium green, and bright. Color (young foliage): upper surface: light green, Yellow-Green Group 146B, and commonly edged with reddish coloration. under surface: light green, Yellow-Green Group 146B, and suffused with reddish brown coloration. Color (adult foliage): upper surface: medium green, Green Group 137A. under surface: medium green, Green Group 137BC.

Inflorescence:

*Number of flowers.*—Usually one to three per stem.

*Penduncle.*—Medium green in coloration, aciculate, and the length is approximately 7 to 8 cm. on average.

*Sepals.*—Upper surface: tomentose, and greenish in coloration. Under surface: medium green in coloration and commonly possess very few extensions.

*Buds.*—Shape: conical and elongated. Length: approximately 2.5 cm. on average. Size: medium. Color upon opening: upper surface: near Yellow-Green Group 154D, and lightly tinted with Yellow-Orange Group 23D. under surface: near Yellow-Green Group 154D, and lightly tinted with Yellow-Orange Group 23D.

*Flower.*—Shape: cup-shaped with reflexed edges. Diameter: approximately 8.5 to 10 cm. on average. Color (when opening begins): upper surface: near Yellow Group 2D, suffused with Yellow-Orange Group 20D, and commonly have a somewhat pearly aspect. under surface: near Yellow Group 2D, suffused with Yellow-Orange Group 20D, and commonly have a somewhat pearly aspect. Color (when blooming): upper surface: near Yellow Group 10D, and more or less suffused with Yellow-Orange Group 20C. under surface: near light Yellow Group 10D, and suffused with light Yellow-Orange Group 20D. Color (at end of opening): upper surface: near Yellow Group 11D, and more or less tinted with Yellow Group 11B. under surface: near Yellow Group 11D, and more or less tinted with Yellow Group 11B. Fragrance: light. Lasting quality: long on the plant and when cut and placed in a vase with the blossoms commonly lasting approximately 10 to 11 days on the plant, and approximately 8 to 10 days in a vase. Petal number: approximately 35 on average. Petal shape: rounded with reflexed edges. Petal drop: good with the petals commonly detaching cleanly. Stamen number: approximately 183 on average. Anthers: normal golden yellow in coloration. Filaments: yellowish in coloration. Pistils: approximately 152 on average. Stigmas: yellowish in coloration. Styles: yellowish in coloration. Receptacle: medium green, smooth, and in longitudinal section in the shape of a pitcher. Hips: hips and seeds are formed.

Development:

*Vegetation.*—Strong.

*Blooming.*—Very abundant with approximately 200 to 300 blooms per square meter commonly being formed per year.

*Resistance to diseases.*—Very good.

I claim:

1. A new and distinct variety of Hybrid Tea rose plant characterized by the following combination of characteristics:

(a) forms in great abundance attractive long-lasting blossoms that are orange-cream in coloration,
(b) exhibits an erect growth habit,
(c) forms attractive medium green and glossy foliage,
(d) exhibits good disease resistance, and
(e) is particularly well suited for cut flower production;

substantially as herein shown and described.

* * * * *